United States Patent
Beyer et al.

(10) Patent No.: US 10,676,454 B2
(45) Date of Patent: Jun. 9, 2020

(54) METHOD FOR PRODUCING MONOMERS FROM ISOMERIC MIXTURES

(71) Applicant: Evonik Operations GmbH, Essen (DE)

(72) Inventors: Silvia Beyer, Ober-Ramstadt (DE); Gaurang Dave, Mumbai (IN); Hans-Jürgen Dillmann, Riedstadt (DE); Volker Herzog, Darmstadt (DE); Joachim Knebel, Alsbach-Hähnlein (DE); Ralf Merbach, Buettelborn (DE); Thorben Schütz, Alsbach-Hähnlein (DE); Martin Trocha, Essen (DE); Sabine Kömmelt, Darmstadt (DE); Patrik Hartmann, Buettelborn (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/074,919

(22) PCT Filed: Jan. 30, 2017

(86) PCT No.: PCT/EP2017/051906
§ 371 (c)(1),
(2) Date: Aug. 2, 2018

(87) PCT Pub. No.: WO2017/134002
PCT Pub. Date: Aug. 10, 2017

(65) Prior Publication Data
US 2019/0031638 A1    Jan. 31, 2019

(30) Foreign Application Priority Data
Feb. 3, 2016  (DE) .......... 10 2016 201 660

(51) Int. Cl.
*C07D 317/24* (2006.01)
*C07D 319/06* (2006.01)
*C08F 220/26* (2006.01)

(52) U.S. Cl.
CPC ......... *C07D 317/24* (2013.01); *C07D 319/06* (2013.01); *C08F 220/26* (2013.01)

(58) Field of Classification Search
CPC .... C07D 317/24; C07D 319/06; C08F 220/26
See application file for complete search history.

(56) References Cited

U.S. PATENT DOCUMENTS

| 4,975,519 A | 12/1990 | Yang et al. |
| 6,008,404 A * | 12/1999 | Miller ............... C07C 67/02 |
| | | 526/173 |
| 9,862,788 B2 | 1/2018 | Hilf et al. |
| 2014/0128536 A1 | 5/2014 | Hilf et al. |

FOREIGN PATENT DOCUMENTS

| DE | 10 2011 109 139 | 2/2013 |
| GB | 690 709 | 4/1953 |
| GB | 690709 | * 4/1953 |
| JP | 2004-018389 | 1/2004 |
| JP | 2004-059435 | 2/2004 |
| JP | 2014-044415 | 3/2014 |

OTHER PUBLICATIONS

Encyclopedia of Polymer Science and Technology, 2010, John Wiley & Sons, Inc. (Year: 2010).*
Díaz-Calleja et al., "Dielectric relaxations in polymers containing dioxacyclohexane rings by thermostimulated depolarization currents," Macromolecular Symposia, vol. 191, 2003, pp. 177-190.
García et al., "Comparative Study of the Mechanical Relaxation Behavior of Polymethacrylates Containing Different Bulky Side Groups," Journal of Polymer Science, Part B, vol. 40(11), 2002, pp. 11554-1162.
H. Minato et al., "Two-stage Polymerization of (1,3-Dioxolan-4-yl)methyl Acrylate," Bulletin of the Chemical Society of Japan, vol. 42, No. 4, 1969, pp. 1146-1148.
García et al., "Comparative study of the relaxation behavior of acrylic polymers with flexible cyclic groups in their structure," Polymer, vol. 41, No. 17, 2000, pp. 6603-6611, Elsevier Science Publishers, Amsterdam, XP004196880.
International Search Report issued in PCT/EP2017/051906 dated Apr. 4, 2017, with English translation.
Written Opinion of the International Searching Authority dated Apr. 4, 2017.

* cited by examiner

*Primary Examiner* — D Margaret M Seaman
(74) *Attorney, Agent, or Firm* — Grüneberg and Myers PLLC

(57) ABSTRACT

A process produces a (meth)acrylate ester mixture. The process includes reacting a glycerol formal isomer mixture with an alkyl (meth)acrylate in the presence of a catalyst.

7 Claims, 1 Drawing Sheet

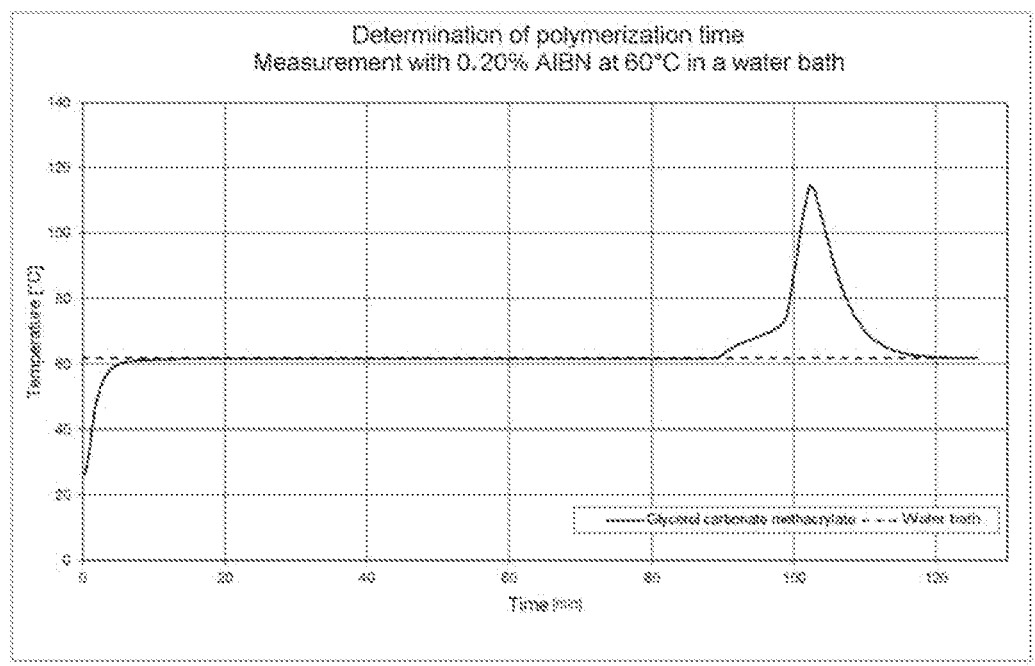

METHOD FOR PRODUCING MONOMERS FROM ISOMERIC MIXTURES

This application is a National Stage entry under § 371 of International Application No. PCT/EP2017/051906, filed on Jan. 30, 2017, and claims priority to European Patent Application No. 10 2016 201 660.1, filed on Feb. 3, 2016.

FIELD OF THE INVENTION

The inversion relates to a process for producing (meth) acrylic esters of isomeric alcohols obtained by reaction of glycerol with formaldehyde (hydroxyl-substituted dioxanes and dioxolanes) in high-yield using titanium-, zirconium- or tin-based catalysts or under base catalysis.

PRIOR ART

The production of (meth)acrylic esters of hydroxyl-modified dioxanes by transesterification is known.

JP 2004018389 describes a process for producing (meth) acrylic esters. The starting material ketalysed glycerol, a 5-membered ring derivative, is reacted with alkyl (meth) acrylate in the presence of titanium or tin catalysts. The obtained (meth)acrylate is then further reacted with water in the presence of a cation exchange resin.

JP 2004059435 describes a similar process for preparing dioxolane compounds. Only primary alcohols (5-membered ring) are described.

The glass transition temperatures of the homopolymers of these 5-membered ring derivatives are about 40° C.

However, for an application for example in floor coatings according to DE102011109139 (Evonik) a high glass transition temperature of the polymer is advantageous here since this ensures a high mechanical robustness. The literature shows that the monomer methacryloyloxy-1,3-dioxane which is derived from the six-membered ring structure is advantageous here since it brings about a glass transition temperature of about 115° C. (Guzman, J. et al. Macromolecular Symposia 2003, 191, 177-190; Guzman, J. J. Polymer Sci. Part B 2002, 40(11), 1154-1162)).

GB 690709 describes a process for producing esters of (meth)acrylic acid and 4-methyloldioxanes and derivatives thereof. An esterification where methacrylic acid is reacted with isomeric alcohols obtained by reaction of glycerol with formaldehyde (hydroxyl-substituted dioxanes and a dioxolanes) is described. In particular, 4-(methacryloyloxymethyl)-1,3-dioxolane is obtained from the glycerol formal isomer mixture by esterification or transesterification with methacrylic acid, methacryloyl chloride or methyl methacrylate.

This forms only the five-membered ring methacrylate although the feedstock consists of the mixture of the five-membered and six-membered ring isomers (about 25:75%). The six-membered ring feedstock proves unreactive, remains unconverted and is removed during the purification of the monomer.

Example 1 intimates that the 1,3-methylideneglycerol present in the isomer mixture of the starting materials is not converted and must therefore be removed by distillation at the end of the reaction.

The same behaviour is observed in the production of 4-(acryloyloxymethyl)-1,3-dioxolane from acrylic acid and glycerol formal isomer mixture by esterification (H. Minato et al. Bull. Chem. Soc. Jpn., 42 (4), 1146 (1969)).

Starting from the industrially available isomer mixture the person skilled in the art is discouraged from performing a reaction to afford the corresponding esters without first removing the less reactive 6-membered ring isomer.

PROBLEM AND SOLUTION

A problem addressed is that of developing a process which overcomes the above-described disadvantages.

Glycerol formal, an isomer mixture composed of 5-membered ring compounds and 6-membered ring compounds, is CMR listed. Glycerol formal methacrylate is not CMR listed. A problem addressed is that of achieving a conversion of the reactant glycerol formal that is as complete as possible.

A problem addressed is that of producing a monomer mixture having a low vapour pressure compared to methyl methacrylate (vapour pressure 3.7 kPa at 20° C., Yaws' Handbook of Antoine Coeff. For Vapour Pressure, Electronic ISBN: 978-1-59124-879-8) or styrene (0.6 kPa at 20° C., Yaws' Handbook of Antoine Coeff. For Vapour Pressure, Electronic ISBN: 978-1-59124-879-8).

A problem addressed is that of providing a homopolymer which exhibits glass transition temperatures comparable to those achieved with the typically used methyl methacrylate and styrene and thus to make replacement of the odourous methyl methacrylate or health-hazardous styrene possible.

Surprisingly, the commercially available glycerol formal affords a (meth)acrylate ester mixture having a high six-membered ring content when the feedstock is reacted with alkyl (meth)acrylate in the presence of a titanium alkoxide, for example isopropyl titanate, a zirconium complex, for example zirconium acetylacetonate, a tin compound such as dioctyltin oxide or a mixture of lithium hydroxide and calcium oxide.

In the context of the present invention glycerol formal describes the isomer mixture of alcohols obtained by the reaction of glycerol with formaldehyde. The commercial isomer mixture employed here has a 5-membered ring:6-membered ring ratio of about 20%:80% to 70%:30%.

It was found that the six-membered ring is present in the (meth)acrylate ester mixture. This guarantees a sufficiently high glass transition temperature of the polymer. The monomer mixture obtained additionally has a very low residual alcohol content.

It was found that the (meth)acrylate obtained according to the invention achieves comparable Tg values of at least 75° C. which make replacement for presently used methacrylates and styrene possible.

It was found that, surprisingly, the vapour pressure of the glycerol formal mixture produced according to the invention is in the order of magnitude of 0.01 hPa at room temperature.

It was found that, surprisingly, the monomer mixtures according to the invention are ideal starting materials for polymers finding use in reactive resins and cold plastics produced therefrom. They feature very good properties, such as longevity, mechanical properties, wear resistance, potentially whiteness or pigmentation and slip resistance, which are all at least as good as for prior art systems. Yet, compared to the prior art, these systems moreover feature particularly low odour formation/release of volatile constituents.

The monomer mixtures according to the invention are outstandingly suitable for polymers employed in coatings, for example floor coatings, paints and lacquers, road markings, casting resins, building protection, composite materials, coating or laminating materials, for example for orthopaedic resins, but also in adhesives.

It was found, surprisingly, that by a transesterification reaction of alkyl (meth)acrylates with isomeric alcohols obtained by reaction of glycerol with formaldehyde (hydroxyl-substituted dioxanes and dioxolanes), particularly advantageously in the presence of titanium-based catalysts, (meth)acrylic esters both of the hydroxyl-substituted dioxanes and of the hydroxyl-substituted dioxolanes can be prepared simultaneously in high yield.

In the process according to the invention alkyl (meth)acrylates are reacted with glycerol formal in the presence of 0.01 to 10 wt %, in particular of 0.1 to 5 wt % based on the total reaction mixture, of a titanium-based catalyst.

BRIEF DESCRIPTION OF THE DRAWING

The FIGURE shows the temperature dependence of the polymerization time of glycerol formal methacrylate with 0.2 wt % of AIBN. The start of the measurement is the time point at which the chosen reaction temperature (T=60° C.) is achieved. The position of the maximum reaction temperature Tmax corresponds to the polymerization time.

REACTANTS AND CATALYSTS

Employable alkyl (meth)acrylates are for example: ethyl (meth)acrylate, n-propyl (meth)acrylate, i-propyl (meth)acrylate, n-butyl (meth)acrylate, i-butyl (meth)acrylate, tert-butyl (meth)acrylate, n-pentyl (meth)acrylate, n-hexyl (meth)acrylate, or preferably methyl methacrylate and butyl acrylate.

The (meth)acrylate notation here is to be understood as meaning both methacrylate, for example methyl methacrylate, ethyl methacrylate, etc., and acrylate, for example methyl acrylate, ethyl acrylate, etc., and also mixtures of both.

The alcohols employed for the transesterification are isomeric alcohols obtained by reaction of glycerol with formaldehyde (hydroxyl-substituted dioxanes and dioxolanes), wherein the ratio of dioxanes to dioxolanes spans from 20:80 to 70:30 mol %.

Suitable catalysts are tin, zirconium or titanium compounds or inorganic bases. Titanium-based transesterification catalysts, in particular tetramethoxy titanium, tetraethoxy titanium, tetraisopropoxy titanium, tetra-n-butoxy titanium, tetrakis(2-ethylhexyloxy) titanium, tetrastearyloxy titanium, may be employed.

Preference is given to catalysts from the group titanium alkoxides, in particular isopropyl titanate, zirconium complexes, in particular zirconium acetylacetonate, tin compounds, in particular dioctyltin oxide, or a mixture of lithium hydroxide and CaO.

The reaction of alkyl (meth)acrylates with isomeric alcohols is performed at temperatures between 30° C. and 180° C., preferably between 50° C. and 130° C. The reaction is effected in the presence of 0.01 to 10 wt %, preferably 0.1 to 5 wt %, particularly preferably 0.2 to 2 wt %, of a catalyst based on the total reaction mixture.

Formally, equimolar amounts of alkyl (meth)acrylate react with the isomeric alcohols to afford the desired end products. However, in practice it is advantageous to maintain an excess of the alkyl (meth)acrylates during the reaction, the alkyl (meth)acrylates being employed in amounts from 1.2 to 15 mol, preferably 2 to 10 mol, per mole of hydroxyl groups.

To avoid yield losses caused by polymerization of the alkyl (meth)acrylates it is advantageous to perform the reaction and workup of the reaction mixture in the presence of polymerization inhibitors.

Polymerization Inhibitors

Polymerization inhibitors are already known. Thus, 1,4-dihydroxybenzenes for example may be added for stabilization. However, differently substituted dihydroxybenzenes may also be employed. In general such inhibitors may be represented by general formula (I)

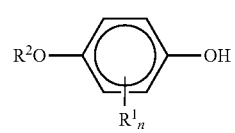

(I)

in which $R^1$ is hydrogen, a linear or branched alkyl radical having one to eight carbon atoms, halogen or aryl, preferably an alkyl radical having one to four carbon atoms, particularly preferably methyl, ethyl, n-propyl, isopropyl, n-butyl, isobutyl, sec-butyl, tert-butyl, Cl, F or Br;

n is an integer in the range from one to four, preferably one or two; and $R^2$ is hydrogen, a linear or branched alkyl radical having one to eight carbon atoms or aryl, preferably an alkyl radical having one to four carbon atoms, particularly preferably methyl, ethyl, n-propyl, isopropyl, n-butyl, isobutyl, sec-butyl or tert-butyl.

However, it is also possible to employ compounds having 1,4-benzoquinone as the parent compound. These may be described by formula (II)

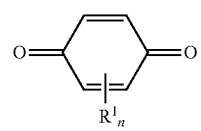

(II)

in which $R^1$ is a linear or branched alkyl radical having one to eight carbon atoms, halogen or aryl, preferably an alkyl radical having one to four carbon atoms, particularly preferably methyl, ethyl, n-propyl, isopropyl, n-butyl, isobutyl, sec-butyl, tert-butyl, Cl, F or Br; and n is an integer in the range from one to four, preferably one or two.

Phenols of general structure (III) are likewise employed.

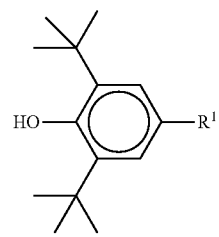

(III)

in which $R^1$ is a linear or branched alkyl radical having one to eight carbon atoms, aryl or aralkyl, propionic esters with 1 to 4 hydric alcohols which may also comprise heteroatoms such as S, O and N, preferably an alkyl radical having one to four carbon atoms, particularly preferably methyl, ethyl, n-propyl, isopropyl, n-butyl, isobutyl, sec-butyl, tert-butyl.

Sterically hindered phenols based on triazine derivatives of formula (IV) represent a further advantageous substance class:

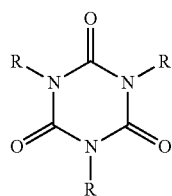

(IV)

where R=compound of formula (V)

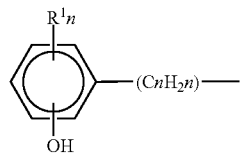

(V)

in which

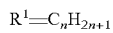

where n=1 or 2.

A further group of known inhibitors are amines, in particular sterically hindered amines.

These include in particular phenylenediamines which may be represented by formula (VI)

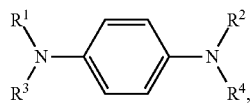

(VI)

in which $R^1$, $R^2$, $R^3$ and $R^4$ are each independently hydrogen and alkyl, aryl, alkaryl, aralkyl radicals each having up to 40, preferably up to 20, carbon atoms, wherein preferably at least one of the radicals $R^1$, $R^2$, $R^3$ and $R^4$ is hydrogen.

Exemplary p-phenylenediamines include p-phenylenediamine wherein the radicals $R^1$, $R^2$, $R^3$ and $R^4$ are hydrogen; N-phenyl-N'-alkyl-p-phenylenediamines, for example N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamines, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine; N-phenyl-N',N'-dialkyl-p-phenylenediamines, for example N-phenyl-N',N'-dimethyl-p-phenylenediamine, N-phenyl-N',N'-diethyl-p-phenylenediamine, N-phenyl-N',N'-di-n-butyl-p-phenylenediamine N-phenyl-N',N'-di-sec-butyl-p-phenylenediamine, N-phenyl-N'-methyl-N'-ethyl-p-phenylenediamine; N,N-dialkyl-p-phenylenediamines, for example N,N-dimethyl-p-phenylenediamine and N,N'-diethyl-p-phenylenediamine; N,N'-dialkyl-p-phenylenediamines, for example N,N'-diisopropyl-p-phenylenediamine, N,N'-diisobutyl-p-phenylenediamine; N,N'-diaryl-phenylenediamines, for example N,N'-diphenyl-p-phenylenediamine; N,N,N'-trialkyl-p-phenylenediamines, for example N,N,N'-trimethyl-p-phenylenediamine, N,N,N'-triethyl-p-phenylenediamine.

Phenazine dyes are moreover a further preferred group. These include induline and nigrosin in particular. Nigrosin is formed by heating nitrobenzene, aniline and aniline acidified with hydrochloric acid with metallic iron and $FeCl_3$. Preference is given here to alcohol-soluble aniline dyes which may comprise for example live benzene nuclei, such as dianilido-N,N-diphenylphenosafranin. These substances are well known and commercially available.

Also suitable are dialkylhydroxylamines, for example N,N-diethylhydroxylamine.

Particularly successfully employed compounds are 1,4-dihydroxybenzene, 4-methoxyphenol, 2,5-dichloro-3,6-dihydroxy-1,4-benzoquinone, 1,3,5-trimethyl-2,4,6-tris(3,5-di-tert-butyl-4-hydroxybenzyl)benzene, 2,6-di-tert-butyl-4-methylphenol, 2,4-dimethyl-6-tert-butylphenol, 2,2-bis[3,5-bis(1,1-dimethylethyl)-4-hydroxyphenyl-1-oxopropoxymethyl]-1,3-propanediyl esters, 2,2'-thiodiethyl bis[3-(3,5-di-tert-butyl-4-hydroxyphenyl)]propionate, octadecyl 3-(3,5-di-tert-butyl-4-hydroxyphenyl)propionate, 3,5-bis(1,1-dimethylethyl-2,2-methylenebis(4-methyl-6-tert-butyl)phenol), tris(4-tert-butyl-3-hydroxy-2,6-dimethylbenzyl)-s-triazine-2,4,6-(1H,3H,5H)trione, tris(3,5-di-tert-butyl-4-hydroxy)-s-triazine-2,4,6-(1H,3H,5H) trione, tert-butyl-3,5-dihydroxybenzene or diphenyl-p-phenylenediamine (DPPD) and also N-oxyl derivatives, for example 4-hydroxy-2,2,6,6-tetramethylpiperidine 1-oxyl, 2,2,5,5-tetramethyl-3-oxopyrrolidine-1-oxyl or 2,2,6,6-tetra, hydroquinone monomethyl ether (4-methoxyphenol) in turn being very particularly appropriate among these.

Particularly preferred inhibitors are phenothiazine, hydroquinone monomethyl ether and 4-hydroxy-2,2,6,5-tetramethylpiperidyl-N-oxyl.

The recited inhibitors are commercially available.

The recited compounds may be employed alone or in mixtures of two or more compounds as basic stabilization for ethylenically unsaturated compounds. Provided that phenolic compounds are concerned, the presence of oxygen in the reaction mixture is required to ensure sufficient efficacy against polymerization. The use of air as the source of this oxygen is particularly preferred.

Solvent

It is moreover possible to perform the reaction in the presence of an inert solvent or of solvent mixtures.

Solvents that may be used include all inert organic solvents, for example aliphatic hydrocarbons, such as hexane, heptane, octane, cyclohexane or mixtures of aliphatic hydrocarbons, for example petroleum ether, ligroin, decalin or benzine.

Aromatic solvents, for example benzene, toluene or the isomeric xylenes and mixtures of the abovementioned compounds, may further be employed.

Also contemplated are oxygen-containing hydrocarbons, for example diethylene glycol monomethyl ether, diethylene glycol monoethyl ether, triethylene glycol monomethyl ether, triethylene glycol monoethyl ether, diethylene glycol monobutyl ether, diethyl ether or methyl tert-butyl ether.

Another contemplated inert solvent is water. Particularly preferably employed solvents are for example toluene or cyclohexane.

The reaction may be performed at atmospheric pressure, underpressure or overpressure and may be conducted in discontinuous or continuous fashion. The reaction is preferably carried out at atmospheric pressure.

Advantageous reaction conditions for removal of the azeotrope are pressures between 1 and 500 hPa.

The reactants alkyl (meth)acrylate and glycerol formal are generally heated to reaction temperature and dewatered together in the presence of an inhibitor or inhibitor mixture. The catalyst/the catalyst mixture and alkyl (meth)acrylate are added after the dewatering step.

The dewatering step may be eschewed depending on the quality of the starting materials. A low water content in the reactants can be tolerated in the reaction.

The eliminated alcohol and the excess alkyl (meth)acrylate are removed by distillation in continuous fashion, preferably together as an azeotrope. The reaction times are generally between 1 and 20 hours, preferably between 2 and 12 hours, and depend on the reaction temperature/on the employed amount of the catalyst.

After termination of the reaction the excess alkyl (meth)acrylate is partly or preferably completely removed from the reaction product, for example by distillative removal.

The product is then separated from the catalyst and further purified via a further distillation. Alternatively, a filtration step may optionally be introduced upstream of the distillation to remove the catalyst. Depending on the requirements for the purity of the reaction product it is also possible to eschew the distillation once the catalyst has been filtered off.

The process according to the invention for producing (meth)acrylic esters by transesterification of alkyl (meth)acrylates with isomeric alcohols obtained by reaction of glycerol with formaldehyde (hydroxyl-substituted dioxanes and dioxolanes) results in markedly higher yields than the processes of the prior art.

The process according to the invention affords monomer mixtures from which homopolymers having a glass transition temperature Tg of >75° C. are obtainable. The glass transition temperatures are preferably in the range between 75° C. and 90° C.

The process according to the invention affords monomer mixtures having a vapour pressure at room temperature of <5 hPa. The vapour pressure at room temperature is preferably 0.001 to 5 hPa, particularly preferably 0.005 to 0.05 hPa.

The examples which follow are intended to elucidate the invention.

EXAMPLES

Example 1: Zirconium-Catalysed Transesterification

The reaction mixture composed of 375 g of glycerol formal, 1009 g of methyl methacrylate (MMA), 0.12 g of hydroquinone monomethyl ether and 0.16 g of phenothiazine is weighed into a 2 L flask fitted with a 50 cm glass column and column packings from Sulzer, a stirring means and an air introduction tube and then heated to boiling point with introduction of air. Any water present is azeotropically removed from the batch with 49 g of distillate. After cooling 11.3 g of $Zr(acac)_4$ and 49 g of MMA are added. The batch is then reheated to boiling point.

The methanol/MMA mixture formed is continuously discharged at a bottoms temperature of 100-120° C. During the reaction, MMA is metered in via a feed in amounts mass-equivalent to the distillate (237 g in total). The reaction is finished after 9:20 h.

Excess MMA and other low boilers are distilled off at a bottoms temperature of 120° C. and 8 mbar of pressure. This affords 645 g of crude ester having a content of the isomeric methacrylic esters of 97.2% and a residual content of the glycerol formal isomers of about 0.3%. After a final fractional distillation 593 g of product are obtained. The proportion of the isomer mixture of 4-(methacryloyloxymethyl)-1,3-dioxolane and 5-methacryloyloxy-1,3-dioxane is 99.8%. The proportion of glycerol formal isomer mixture is 0.14%.

Example 2: Titanium-Catalysed Reaction

The reaction mixture composed of 29.1 kg of glycerol formal, 78.5 kg of methyl methacrylate (MMA), 9.6 g of hydroquinone monomethyl ether, 1.4 g of 4-hydroxy-2,2,6,6-tetramethylpiperidine 1-oxyl, 2.8 g of N,N-diethylhydroxylamine (85% w/w in water) and 12 g of phenothiazine is weighed into a 145 L enamel vessel fitted with a 4.5 m NW150 glass column and column packings from Sulzer, a stirring means and an air introduction tube without catalyst and then heated to boiling point with introduction of air using an oil circulation thermostat. The batch is dewatered with 1700 g of distillate with a low reflux ratio without temperature limitation. Once a constant column-top temperature of 99° C. is achieved the dewatering step is terminated.

729 g of isopropyl titanate and 1700 g of MMA are added. The methanol/MMA mixture formed is continuously discharged at a bottoms temperature of 100-120° C. During the reaction, MMA is metered in via a feed in amounts mass-equivalent to the distillate (12.6 kg in total). After 8:30 h the column-top temperature slowly increases and after 9:30 hours a temperature in the column top of 99° C. is achieved. The reaction is finished when the temperature in the column top exceeds 99° C. and then remains constant.

To remove the excess MMA, the batch is now brought to boiling point at a pressure of 350 mbar and methyl methacrylate is removed by distillation while the pressure is continuously reduced in order to maintain a bottoms temperature of 75-85° C. When a pressure of 32 to 38 mbar has been achieved the batch is held at 85° C. for 45 min. in total, 58.35 kg of methyl methacrylate are obtained. The catalyst-containing crude ester remaining in the bottoms comprises 48.2 kg and consists of 94.5% of isomer mixture of 4-(methacryloyloxymethyl)-1,3-dioxolane and 5-methacryloyloxy-1,3-dioxane, 2.8% of MMA and 1.22% of glycerol formal isomer mixture. Said crude ester may be freed of catalyst and thus further purified by distillation at 0.4-0.5 mbar and an oil circulation temperature of 165-170° C. in an NGW DS50 thin-film evaporator. The distillate consists of the isomeric methacrylic esters and has a purity determined by gas chromatography of 98.6%. The proportion of the glycerol formal isomers is 0.68%.

The glass transition temperature of the isomer mixture is 75° C. This value shows that both the 5-membered ring and the 6-membered ring of the isomer mixture were converted.

Example 3: Tin-Catalysed Transesterification

The reaction mixture composed of 375 g of glycerol formal. 1009 g of methyl methacrylate (MMA), 0.12 g of hydroquinone monomethyl ether and 0.16 g of phenothiazine is weighed into a 2 L flask fitted with a 50 cm glass column and column packings from Sulzer, a stirring means and an air introduction tube and then heated to boiling point with introduction of air. Any water present is azeotropically removed from the batch with 60 g of distillate. After cooling 18.8 g of dioctyltin oxide and 60 g of MMA are added. The batch is then reheated to boiling point.

The methanol/MMA mixture formed is continuously discharged at a bottoms temperature of 100-120° C. During the reaction, MMA is metered in via a feed in amounts mass-equivalent to the distillate (275 g in total). The reaction is finished after 11:00 h.

Excess MMA and other low boilers are distilled off at a bottoms temperature of 120° C. and 8 mbar of pressure. This affords 550 g of crude ester having a content of the isomeric methacrylic esters of 95.6% and a residual content of the glycerol formal isomers of about 0.3%. After a final fractional distillation 490 g of product are obtained. The proportion of the isomer mixture of 4-(methacryloyloxymethyl)-1,3-dioxolane and 5-methacryloyloxy-1,3-dioxane is 98.25%. The proportion of glycerol formal isomer mixture is 0.17%.

Example 4: Base-Catalysed Transesterification

The reaction mixture composed of 5.6 kg of glycerol formal, 12.5 of methyl methacrylate (MMA), 1.9 g of hydroquinone monomethyl ether and 19.7 g of CaO and 8.4 g of LiOH as catalyst is weighed into a 20 L vessel fitted with a 1 m NW50 glass column and column packings from Sulzer, a stirring means and an air introduction tube and then heated to boiling point with introduction of air.

The methanol/MMA mixture formed is continuously discharged at a bottoms temperature of 100-120° C. During the reaction, MMA is metered in via a feed in amounts mass-equivalent to the distillate (3.5 kg in total). After about 5 h reaction time, 9.8 g of CaO and 4.2 g of LiOH and 200 g of MMA are added. The reaction is finished after 11:30 h.

Excess MMA and other low boilers are distilled off initially in the vessel and then in the thin-film evaporator (5-6 mbar, 110° C. oil circulation temperature 110° C.). After a final pressure filtration, 8 kg of a mixture of the isomeric methacrylic esters having a purify of 94.7% determined by gas chromatography are obtained. The proportion of the glycerol formal isomers is 0.96%.

Example 5: Slab Polymerization Procedure 200 g of glycerol formal methacrylate were initiated with 0.1% azobis(isobutyronitrile) (AIBN) and fitted into a glass chamber (25×25 cm; 0.4 cm shrink cord). The chamber was airtightly sealed and polymerized in a wafer bath (12 h 50° C.: 3 h 60° C.) and subsequently heat-treated in a drying cabinet at 90° C. for 2 hours. The produced polyglycerol formal methacrylate homopolymer was subsequently utilized for determining the glass transition temperature.

Example 6: DSC Measurement (Determination of Glass Transition Temperature)

To determine glass transition temperature the commonly used analytical method differential scanning calorimetry (DSC) was used (Ehrenstein, Gottfried W. Riedel, Gabriela, Trawiel, Pia (2004); Thermal Analysis of Plastics—Theory and Practice; Hanser Publishers).

The specimen produced by slab polymerization (see example 5) was analysed under nitrogen over the temperature range of −50° C. to 150° C. with a heating rate of 10K/min (rapid cooling) in an aluminium crucible having a perforated lid (Mettler Toledo DSC instrument with liquid nitrogen cooling).

Determined polyglycerol formal methacrylate glass transition temperature: Tg=85° C.

Example 7: Polymerization Time Determination (PT Measurement)

To determine polymerization time 0.2 wt % of AIBN (CAS 78-67-1) were weighed in and dissolved in the glycerol formal methacrylate monomer. This mixture was homogenized for 2 min with a magnetic stirrer, transferred into a test tube (18×180 mm), heated to T=60° C. in a water bath and the polymerization time was subsequently measured. The temperature profile of the reaction was plotted using a temperature probe. This temperature probe is located in a second, smaller tube filled with diethylene glycol as carrier liquid which is secured in the centre of the test tube such that it is immersed into the sample liquid to a sufficient depth to allow precise measurement of the sample temperature. The start of the measurement is the time point at which the chosen reaction temperature (T=60° C.) is achieved. The position of the maximum reaction temperature $T_{max}$ corresponds to the polymerization time.

Glycerol Formal Methacrylate PT Measurement

| Initiator: | Time [min] | 102.5 |
|---|---|---|
| 0.2% AIBN | $T_{max}$ [° C.] | 114.5 |
| T = 60° C. | | |

Example 8: Vapour Pressure Determination (Dynamic Method Using Ebulliometer)

The vapour pressure data were determined with the dynamic method using an ebulliometer (developed by LTP GmbH for small sample quantifies from about 20 mL in accordance with EU guideline: Dynamic Method of the EC A.4 Vapour Pressure guideline based on OECD guideline 104).

Experimental Data: Glycerol Formal Methacrylate Vapor Pressure

| T [° C.] | Pressure [hPa] |
|---|---|
| 56.45 | 0.53 |
| 64.16 | 1 |
| 71.33 | 1.8 |
| 80.89 | 3.4 |
| 90.35 | 6.5 |
| 96.96 | 9.4 |
| 108.95 | 17.5 |
| 122.31 | 33.9 |
| 134.72 | 58.4 |
| 144.76 | 88.9 |
| 195.88 | 479.3 |
| 201.10 | 551.3 |
| 208.21 | 654.0 |
| 215.35 | 778.8 |
| 224.18 | 697.3 |
| 226.17 | 1004.1 |

Antoine Parameters (DDB Format) for Glycerol Formal Methacrylate $\log(P/\text{Torr}) = A - B/(C + T/°\text{C.})$

| A | B | C |
|---|---|---|
| 6.39262 | 1232.98 | 125.136 |

Vapour pressure at T=20° C. for glycerol formal methacrylate (extrapolated from Antoine parameter):
p=0.01 hPa

The invention claimed is:

1. A process for producing a (meth)acrylate ester mixture, the process comprising:
    reacting a glycerol formal isomer mixture with an alkyl (meth)acrylate in the presence of a catalyst.
2. The process according to claim 1, wherein
    the glycerol formal isomer mixture is a mixture having an isomer ratio of 5-membered ring isomer to 6-membered ring isomer of 20:80 to 70:30.
3. The process according to claim 2, wherein
    a homopolymer, comprising reacted units of at least one (meth)acrylate ester isomer from the (meth)acrylate ester mixture, has a glass transition temperature Tg of from 75° C. and 90° C.
4. The process according to claim 1, wherein
    the catalyst is at least one member selected from the group consisting of a titanium alkoxide, a zirconium complex, a tin compound, and a mixture of lithium hydroxide and calcium oxide.
5. The process according to claim 1, wherein
    said reacting is performed at a temperature of from 30° C. and 180° C.
6. A (meth)acrylate ester mixture obtained by a process according to claim 1, wherein the (meth)acrylate ester has a vapor pressure of from 0.001 and 5 hPa which comprises (meth)acrylic esters of hydroxyl-substituted dioxanes and hydroxyl-substituted dioxolanes.
7. A process of producing a polymer, the process comprising:
    polymerizing the (meth)acrylate ester mixture according to claim 6.

* * * * *